United States Patent
Lombardo et al.

(10) Patent No.: US 8,409,252 B2
(45) Date of Patent: Apr. 2, 2013

(54) KNOTLESS SUTURE ANCHOR

(75) Inventors: Giuseppe Lombardo, New Port Richey, FL (US); Steven E. Fitts, Largo, FL (US)

(73) Assignee: Linvatec Corporation, Largo, FL (US)

( * ) Notice: Subject to any disclaimer, the term of this patent is extended or adjusted under 35 U.S.C. 154(b) by 573 days.

(21) Appl. No.: 12/487,280

(22) Filed: Jun. 18, 2009

(65) Prior Publication Data

US 2009/0318964 A1    Dec. 24, 2009

Related U.S. Application Data

(63) Continuation-in-part of application No. 12/079,097, filed on Mar. 25, 2008, now Pat. No. 8,162,978.

(51) Int. Cl.
*A61B 17/04* (2006.01)

(52) U.S. Cl. ...................................... 606/232

(58) Field of Classification Search .................. 606/53, 606/232, 300, 301, 313; 411/999, 21, 22; 623/13.11, 13.14

See application file for complete search history.

(56) References Cited

U.S. PATENT DOCUMENTS

| | | | | | |
|---|---|---|---|---|---|
| 5,643,321 | A | * | 7/1997 | McDevitt | 606/232 |
| 5,702,215 | A | * | 12/1997 | Li | 411/21 |
| 5,843,127 | A | * | 12/1998 | Li | 606/232 |
| 5,849,004 | A | * | 12/1998 | Bramlet | 606/232 |
| 5,935,129 | A | * | 8/1999 | McDevitt et al. | 606/232 |
| 6,022,373 | A | * | 2/2000 | Li | 606/232 |
| 6,527,794 | B1 | * | 3/2003 | McDevitt et al. | 606/232 |
| 6,692,516 | B2 | * | 2/2004 | West et al. | 606/232 |
| 6,695,844 | B2 | * | 2/2004 | Bramlet et al. | 606/66 |
| 6,932,834 | B2 | * | 8/2005 | Lizardi et al. | 606/232 |
| 7,837,710 | B2 | * | 11/2010 | Lombardo et al. | 606/232 |
| 2006/0116719 | A1 | * | 6/2006 | Martinek | 606/232 |
| 2006/0235413 | A1 | * | 10/2006 | Denham et al. | 606/72 |
| 2007/0093858 | A1 | * | 4/2007 | Gambale et al. | 606/142 |
| 2007/0270907 | A1 | * | 11/2007 | Stokes et al. | 606/232 |
| 2009/0099598 | A1 | * | 4/2009 | McDevitt et al. | 606/232 |

* cited by examiner

*Primary Examiner* — Corrine M McDermott
*Assistant Examiner* — Todd J Scherbel

(57) ABSTRACT

An anchoring device for deployment in a pre-formed hole to secure soft tissue to bone. Embodiments of the anchoring device include an outer member and an inner member that moves relative to the outer member from a suture-unlocked position to a suture-locked position. The inner member further includes an elongated projection with a proximal end that defines an outer dimension. In one embodiment, the elongated projection is configured to interface with a portion of the outer member so as to change the outer dimension in a manner that causes the elongated projection to displace a portion of the bone.

18 Claims, 7 Drawing Sheets

KNOTLESS SUTURE ANCHOR

CROSS REFERENCE TO RELATED APPLICATIONS

This application is a continuation-in-part of, and claims the benefit of priority from U.S. patent application Ser. No. 12/079,097, now U.S. Pat. No. 8,162,978, entitled "Nonmetallic Knotless Suture Anchor," and filed on Mar. 25, 2008, the content of which application is incorporated herein by reference in its entirety.

FIELD OF THE INVENTION

The present invention is related to anchors for securing material to soft tissue and bone, and more particularly embodiments of the present invention relate to suture anchors for knotlessly securing filamentary materials, and soft tissue at a surgical site.

BACKGROUND OF THE INVENTION

Suture anchors are commonly employed during surgical procedures to secure soft tissue to bone. Such anchors are generally inserted into a pre-formed hole in the bone, so that a portion of filamentary material (e.g., suture material) extends out of the hole from the anchor. Suture material, as the term is used and described herein, include monofilament or multi-filament suture as well as any other metallic or non-metallic filamentary or wire-like material suitable for performing the function of a suture. This material can include both absorbable and non-absorbable materials.

For open and closed surgical procedures, the suture material is tied to the soft tissue in a manner that forms a knot. But for surgical procedures that are typically closed, including those procedures performed arthroscopically or endoscopically, the knot is often difficult to form. Suture anchors that do not require a knot, also referred to as "knotless suture anchors," have been developed to avoid the step of tying the knot.

One example of a knotless suture anchor is shown in U.S. Pat. No. 6,692,516 to West Jr. et al., assigned to the assignee hereof and incorporated by reference in its entirety herein. There is provided here an expandable metallic knotless suture anchor, which is difficult to implement in the form of non-metallic material. Another example is shown in U.S. Patent Application Publication No. 2005/0055052 filed by Lombardo et al., and assigned to the assignee hereof and incorporated by reference in its entirety herein. This application discloses a knotless suture anchor that is constructed of bioabsorbable material, but may be limited in its application to certain surgical procedures.

This limitation to certain surgical procedures is unfortunate because other procedures, including rotator cuff repairs, would benefit from knotless suture anchors, and more particularly, from a knotless suture anchor that is secured to the cancellous bone. It would be likewise beneficial if the knotless suture anchor is provided so as to prevent the tendency to migrate above the cortical layer of the bone, as well as from the level of the humeral head or other bone at the anchor site.

Therefore, there is a need for a knotless suture anchor that is compatible with a wide range of surgical procedures. There is likewise a need that the proposed knotless suture anchor is configured to engage not only the cancellous bone, but also to engage the bone in a manner that prevents migration of the anchoring device.

SUMMARY OF THE INVENTION

The present invention relates generally to an apparatus, system, and method by which certain surgical procedures that normally secure soft tissue proximate bone with knotted sutures, are accomplished in a manner that substantially reduces the need for knots, and knotted sutures to position the soft tissue as desired. For example, there is provided an anchoring device that can knotlessly secure material to bone, and as discussed in more detail below, to engage the cortical layer of bone so as to secure the device in the cancellous bone below the cortical layer. Embodiments of the anchoring device that are made in accordance with the concepts of the present invention are configured to expand inside of a pre-formed hole in the bone, displace the cancellous bone from the hole, and engage the lower portion of the cortical layer proximate the cancellous bone.

BRIEF DESCRIPTION OF THE DRAWINGS

So that the manner in which the above recited features of the present invention can be understood in detail, a more particular description of the invention briefly summarized above, may be had by reference to the figures, some of which are illustrated and described in the accompanying appendix. It is to be noted, however, that the appended documents illustrate only typical embodiments of this invention and are therefore not to be considered limiting of its scope, for the invention may admit to other equally effective embodiments. Moreover, the drawings are not necessarily to scale, with emphasis generally being placed upon illustrating the principles of certain embodiments of invention.

Thus, for further understanding of the nature and objects of the invention, references can be made to the following detailed description, read in connection with the specification following below in which.

DETAILED DESCRIPTION OF THE INVENTION

With reference to the figures in general, and FIGS. 1-7 in particular, there is provided an anchoring device, and system for deploying the same, embodiments of which are configured so that in its deployed state, the anchoring device displaces the cancellous layer of bone in a pre-formed hole, and engages the cortical layer of bone. Devices such as those disclosed and described herein include inner and outer members that are insertably engaged so as to permit relative movement of the members from a suture-unlocked position, to a suture-locked position. This secures suture material between the inner and outer members. It does not, however, cause the length of the suture material to change as the relative positions of the inner and outer member of the anchor are changed from the suture-unlocked position to the suture-locked position. Nor does it alter the axis of compression, so that tension that is applied to the suture material during the surgical procedure is maintained at a substantially consistent level when actuating the anchoring device from its suture-unlocked to suture-locked position in the bone.

While details of the construction of the inner and outer members, and embodiments of the anchoring device generally are provided below, it may be desirable that each can comprise biocompatible materials, which are sufficiently resilient, and which permit the relative movement of the inner and outer members. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra high molecular weight polyethylene ("UHMWPE"), as well as other metallic, non-metallic, and polymeric materials. In some embodiments of the anchoring device, the materials that are selected for the inner and outer members may have physical properties that are consistent with, or compatible with certain performance factors for the anchoring device. These factors include, for example, tensile strength, shear strength, and flexibility of all or part of the anchoring device, as well as any combinations thereof. Each of the factors mentioned above, and contemplated herein may be determined in connection with the configuration of the inner and outer members, as well as in conjunction with the changes in the anchoring device as the relative positions of the inner and outer members change from the suture-unlocked position to the suture-locked position.

Figure 1:
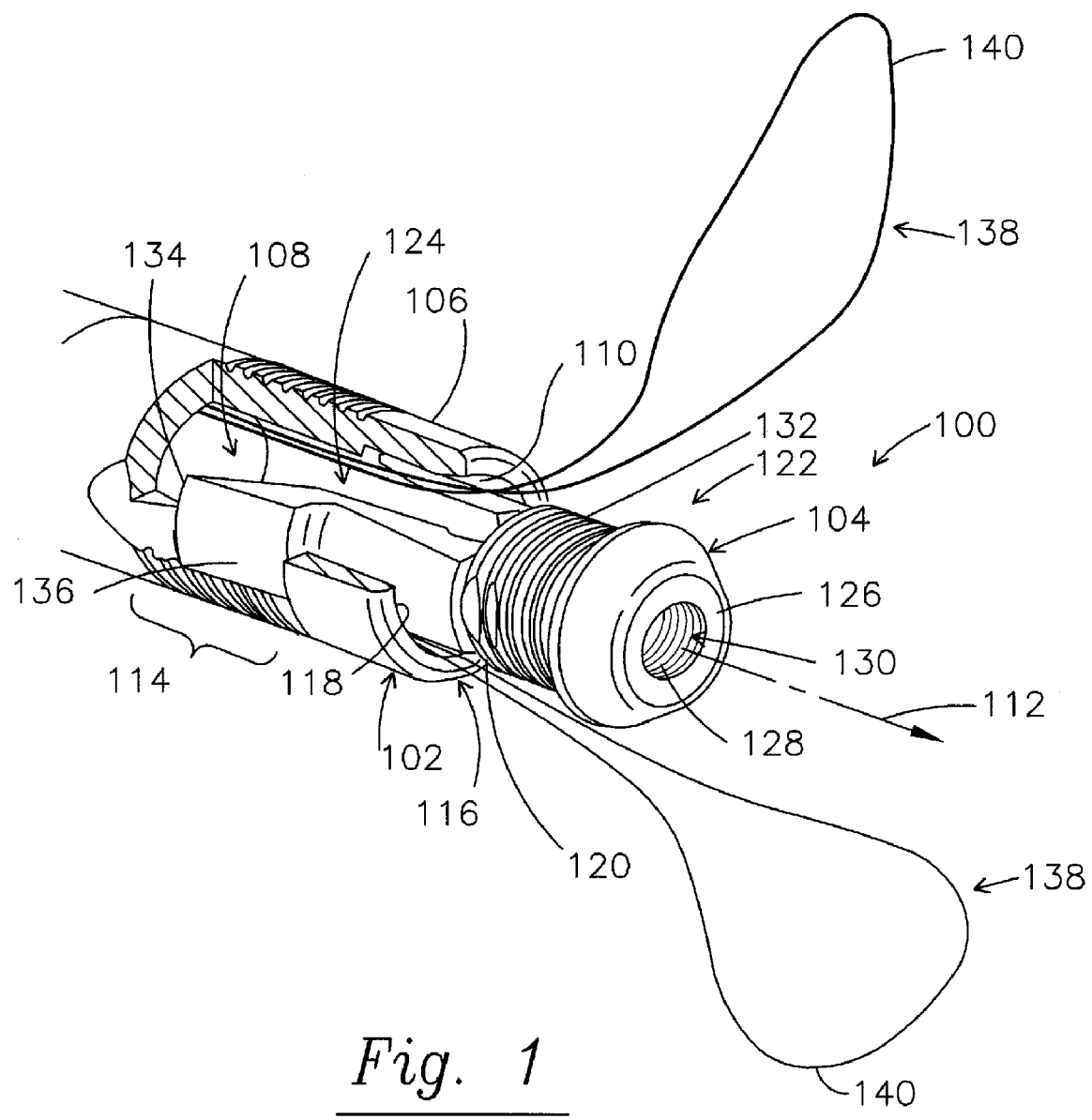
FIG. 1 is a perspective view of one embodiment of an anchoring device that is made in accordance with concepts of the present invention, the anchoring device being disposed on the distal end of an actuator device, and in a suture-unlocked position.

Referring now to FIG. 1, an embodiment of an anchoring device 100 that is made in accordance with concepts of the present invention is illustrated. The anchoring device 100 comprises an outer member 102, and an inner member 104 that is arranged in the present example relative to the outer member 102 in a suture-unlocked position. The outer member 102 includes a substantially cylindrical body 106 that has an axial lumen 108, which has an inner suture surface 110, and a longitudinal axis 112. The cylindrical body 106 also includes an aperture 114, and an outer member distal end 116 with an opening 118 that is sized and configured to receive the inner member 104 as described herein.

The inner member 104 comprises an elongated body 120 that has a distal portion 122 and a proximal portion 124 that extends away from the distal portion 122. The distal portion 122 includes an inner member distal end 126 with a distal lumen 128, and an opening 130 that provides access to the distal lumen 128. The distal portion 122 also includes an outer suture surface 132.

The proximal portion 124 includes a proximal end 134 with an outer dimension, and in the case of the elongated body 120, the outer dimension is the diameter of the elongated body 120 as measured at the proximal end 134. The proximal portion 124 also includes an elongated projection 136 that extends from the distal portion 122 to the proximal end 134. The elongated projection 136 is constructed so as to cause the diameter of the proximal end 134 to change when the inner member 104 moves relative to the outer member 102.

For example, and as described in more detail in connection with FIGS. 2 and 3 below, the elongated projection 136 is configured for radial movement away from the longitudinal axis 112 in response to the relative movement of the outer member 102 and the inner member 104. This changes the outer dimension of the proximal end 134. This can also cause the elongated projections 136 to engage the cancellous bone in the pre-formed hole, and in one construction of the inner member 104 the elongated projection 136 protrudes out of the aperture 114 so as to cause the proximal end 134 to engage the cortical layer of bone as the anchoring device 100 is deployed from the suture-unlocked position to the suture-locked position.

Continuing with this discussion of the deployment of the anchoring device 100 in more detail, it is noted that the anchoring device 100 in the example of FIG. 1 includes suture material 138, which is positioned between the inner suture surface 110 and the outer suture surface 132. The suture material 138 includes loops 140 that are sized so as to engage other suture material, and/or soft tissue. In one example, the suture material 138 is positioned in the anchoring device 100 during the surgical operation with one or more snares (not shown) that are positioned so that the suture material 138 is drawn into the anchoring device 100, and more particularly between the outer member 102 and the inner member 104. In another example, the suture material 138 is pre-positioned in the anchoring device 100 so as to facilitate its deployment during the surgical procedure.

Notwithstanding the mode in which the suture material 138 is disposed in the anchoring device 100, and continuing with the discussion of the deployment, the anchoring device 100 is inserted into the pre-formed hole in the bone so that the loops 140 extend out of the hole and at a position to engage, e.g., the suture material, and/or the soft tissue. Once engaged as desired, the inner member 104 is moved relative to the outer member 102 along the longitudinal axis 112. This compresses the suture material 138 between the inner suture surface 110 and the outer suture surface 132. A more particular example of the deployment of anchoring devices like the anchoring device 100 can be had with reference to FIGS. 2 and 3 below.

Figure 2:
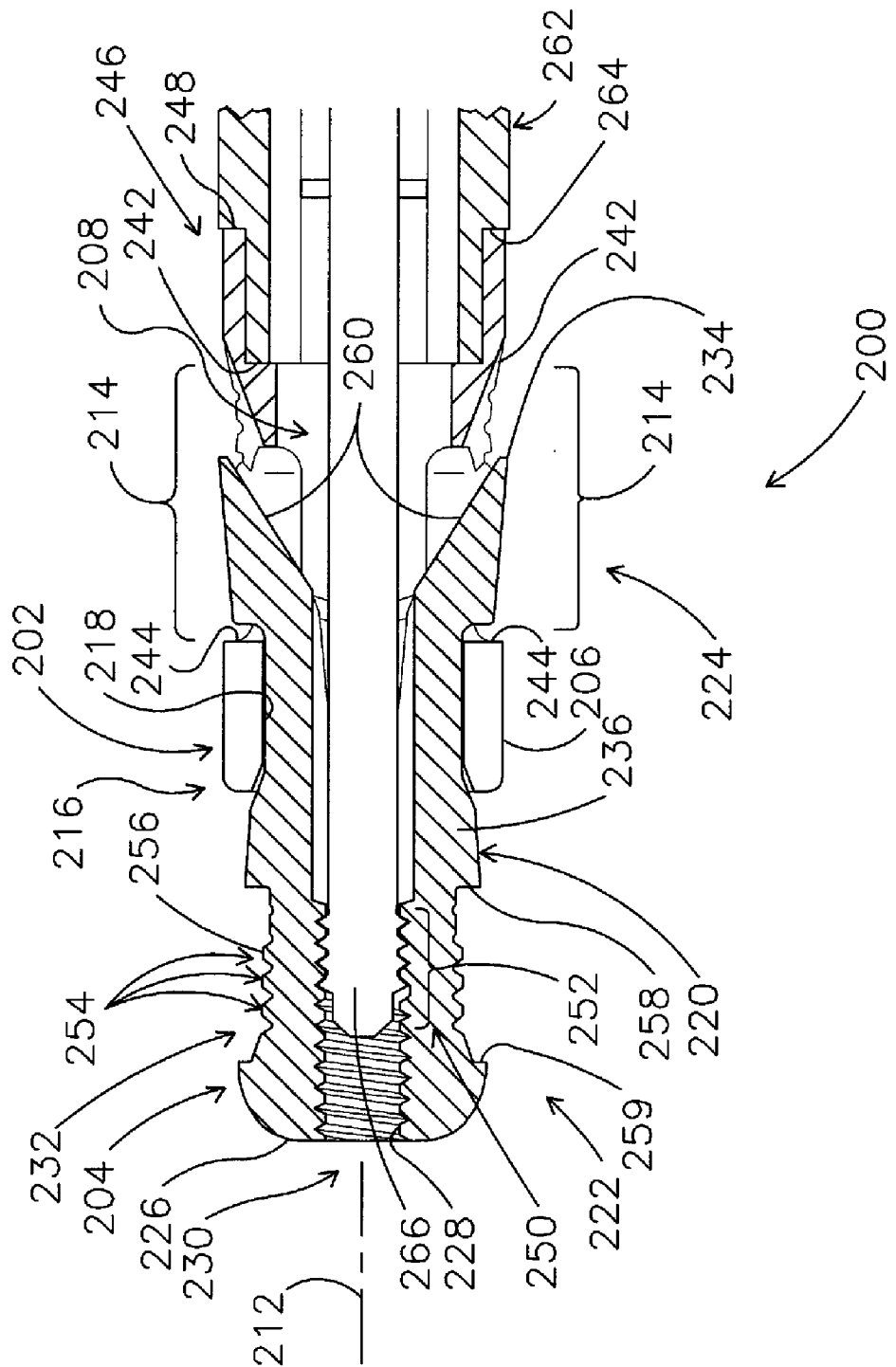
FIG. 2 is a cross-sectional, side, plan view of another embodiment of an anchoring device that is made in accordance with the concepts of the present invention, the anchoring device in a suture-unlocked position.
Figure 3:
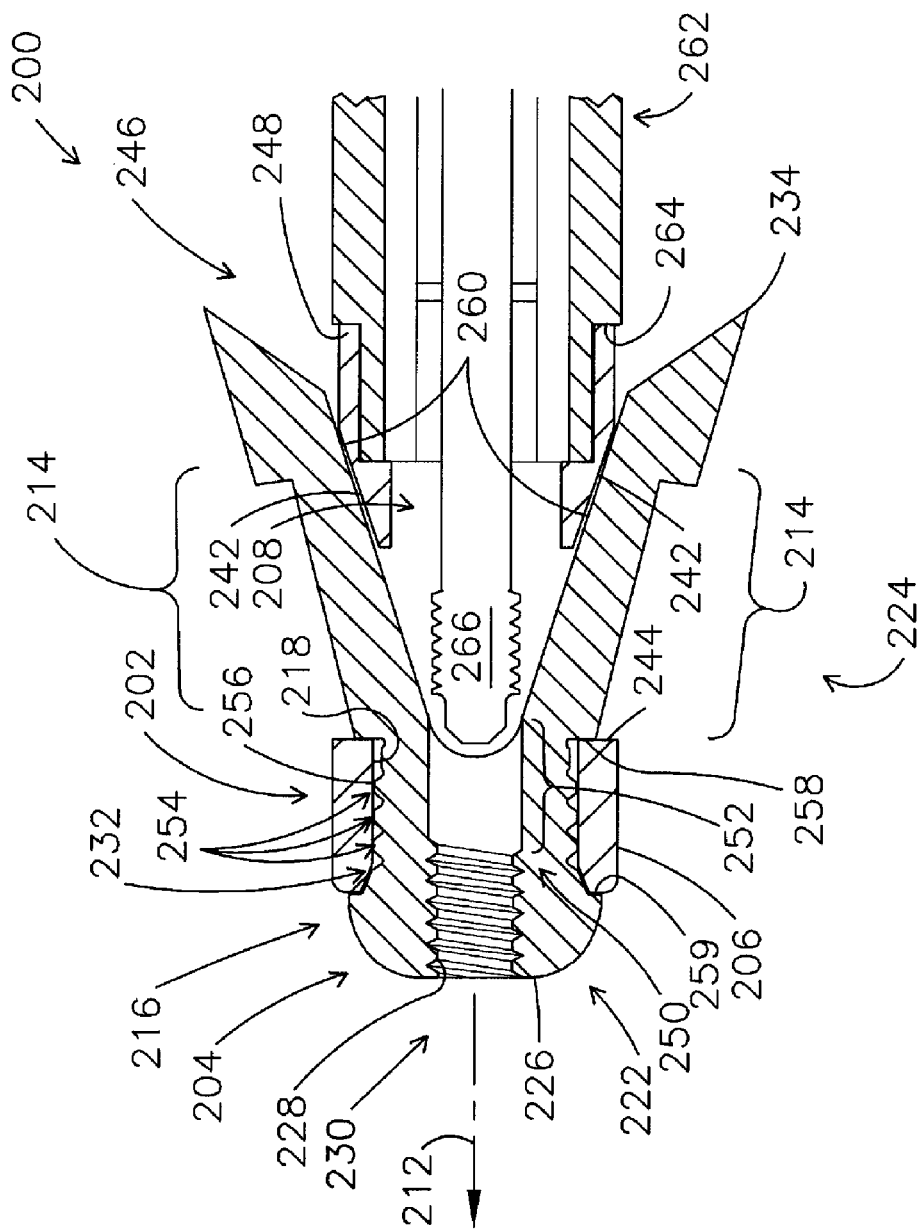
FIG. 3 is a cross-section, side, plan view of the embodiment of the anchoring device of FIG. 2 in a suture-locked position.

For example, and with reference now to FIGS. 2 and 3, a cross-sectional view of another embodiment of an anchoring device 200 is illustrated. It is noted that like numerals are used to identify like components that are found in FIG. 1, but the numbers are increased by 100. For example, and with reference first to FIG. 2, the anchoring device 200 comprises an outer member 202, and an inner member 204 that is positioned relative to the outer member 202 in a suture-unlocked position.

Without recitation of all of the similar parts of the anchoring device 200, it is seen in this example that the cylindrical body 206 of the outer member 202 includes a pair of apertures 214 that each has a ramped portion 242, which tapers substantially outwardly away from the longitudinal axis 212. The apertures 214 also have an aperture end surface 244 that is located on the side of the aperture 214 opposite the ramped portion 242. The cylindrical body 206 further includes an outer member proximal end 246 that has an end surface 248, which is on the end of the cylindrical body 206 that is opposite of the outer member distal end 216.

The elongated body 220 of the inner member 204 further comprises a distal portion 222 and a proximal portion 224. Moreover, the distal portion 222 includes a distal lumen 230 that has a frangible portion 250, which has a material disengagement area 252 that extends from the proximal portion 224 into the distal lumen 230. The distal portion 222 also includes an outer suture surface 232 that has a plurality of suture compression projections 254 with a projection surface 256.

The proximal portion 222 includes a proximal end 234, and a pair of elongated projections 236, which extend from the proximal ends 234 to a step 258 that bounds the outer edge of the outer suture surface 232. A secondary step 259 is included that bounds the other edge of the outer suture surface 232. Each of the elongated projections 236 have an engagement surface 260, which tapers substantially inwardly from the proximal end 234 toward the longitudinal axis 212.

In the present example, the anchoring device 200 is coupled to an actuator device 262, and more particularly the actuator device 262 includes mating surface 264 in communication with the end surface 248 of the outer member. The actuator device 262 also includes a mandrel 266 that is coupled to the material disengagement area 252. In one example, this connection comprises one or more complimentary threaded surfaces on the material disengagement area 252, and on the mandrel 266. In another example, one or more of the material disengagement area 252, and the mandrel 266 can include a mechanical interface (not shown) that can engage a similar, or complimentary mechanical interface on the opposing part of the anchoring device 200. Examples of suitable implements for use as the mechanical interface include, but are not limited to, a key-and-slot arrangement, shearable fasteners, adhesives, and tapes, among other devices, and methods for securing the material disengagement area 252 and the mandrel 266.

In one embodiment, the connection between the material disengagement area 252, and the mandrel 266 is configured to release, or "break away," when a force applied by the actuator device 262 reaches and/or exceeds a threshold level. For example, as it is illustrated in the suture-locked position of FIG. 3, this force may shear the threaded surface of one or both of the material disengagement area 252 and the mandrel 264. While the threshold level can be determined in accordance with a number of factors (including materials of construction, the type or arrangement of the mechanical interface, etc.), the force is generally less than about 280 N, and in one example the force is from about 180 N to about 250 N. In one embodiment of the anchoring device 200, the material disengagement area 252 and the mandrel 266 each have threaded surfaces with threads of about 80 threads per inch, and with about 0.8 mm to about 2 mm of threads that are engaged along the two threaded surfaces.

With continued reference to FIG. 3, in other embodiments of the anchoring device 200, the threshold level may be selected so as to permit the actuator device 262 to deploy the anchoring device 200 from the suture-unlocked position (of FIG. 2) to the suture-locked position (of FIG. 3), before the release of the connection between the material disengagement area 252 and the mandrel 266. In one example, the actuator device 262 can cause the inner member 202 to move in relation to the outer member 204 so as to cause the engagement surfaces 256 of the elongated projections 236 to engage the ramped portions 242. This, in turn, urges the elongated projections 236 outwardly, and away from the longitudinal axis 212, in a manner that changes the outer dimension of the proximal end 234 from a first dimension (in the suture-unlocked position) to a second dimension (in the suture-locked position). In one example, the difference between the first dimension and the second dimension is from about 6 mm to about 9 mm.

In one embodiment, the anchoring device 200 is maintained at this second dimension by the engagement of the outer member 202 and the inner member 204. In one example, the step 258 engages with the aperture end surfaces 244. In another example, a portion of the outer member distal end 216 engages the secondary step 259, and the aperture end surface 244 engages the step 258.

In the suture-locked position, the suture material (not shown) is compressed between the inner suture surface 210, and one or more of the engagement surfaces 256. Each of the inner suture surface 210 and the engagement surfaces 256 can have, respectively, an inner diameter and an outer diameter that is dependent on the amount of compression of the suture material, as a percentage of the diameter of the suture material. This is typically dependent upon the suture material, but is estimated to be on the order of from about 70% to about 80%, and may in some embodiments be from about 50% to about 90%. Likewise, the amount of suture material that is compressed between the inner suture surface 210 and the engagement surfaces 256, also considered the length of the compressed suture material, is generally less than about 4 mm, and more typically from about 2 mm to about 3 mm.

It is also noted that in the dimensions and the tolerances of the outer member 202 and the inner member 204 in many embodiments of the present invention are such that as the inner member 204 moves relative to the outer member 202, they may deform out of concentricity when the suture material is compressed only at two diametrically opposed locations. In one example, the locations are spaced at about 90° from the position of the suture material, e.g., the position of the projections 236 on the inner member 204, and generally not subject to the same stresses and may not be deformed to the same extent. The extent of the deformation is well within the degree of resilience of the materials of construction contemplated and discussed herein.

Figure 4:
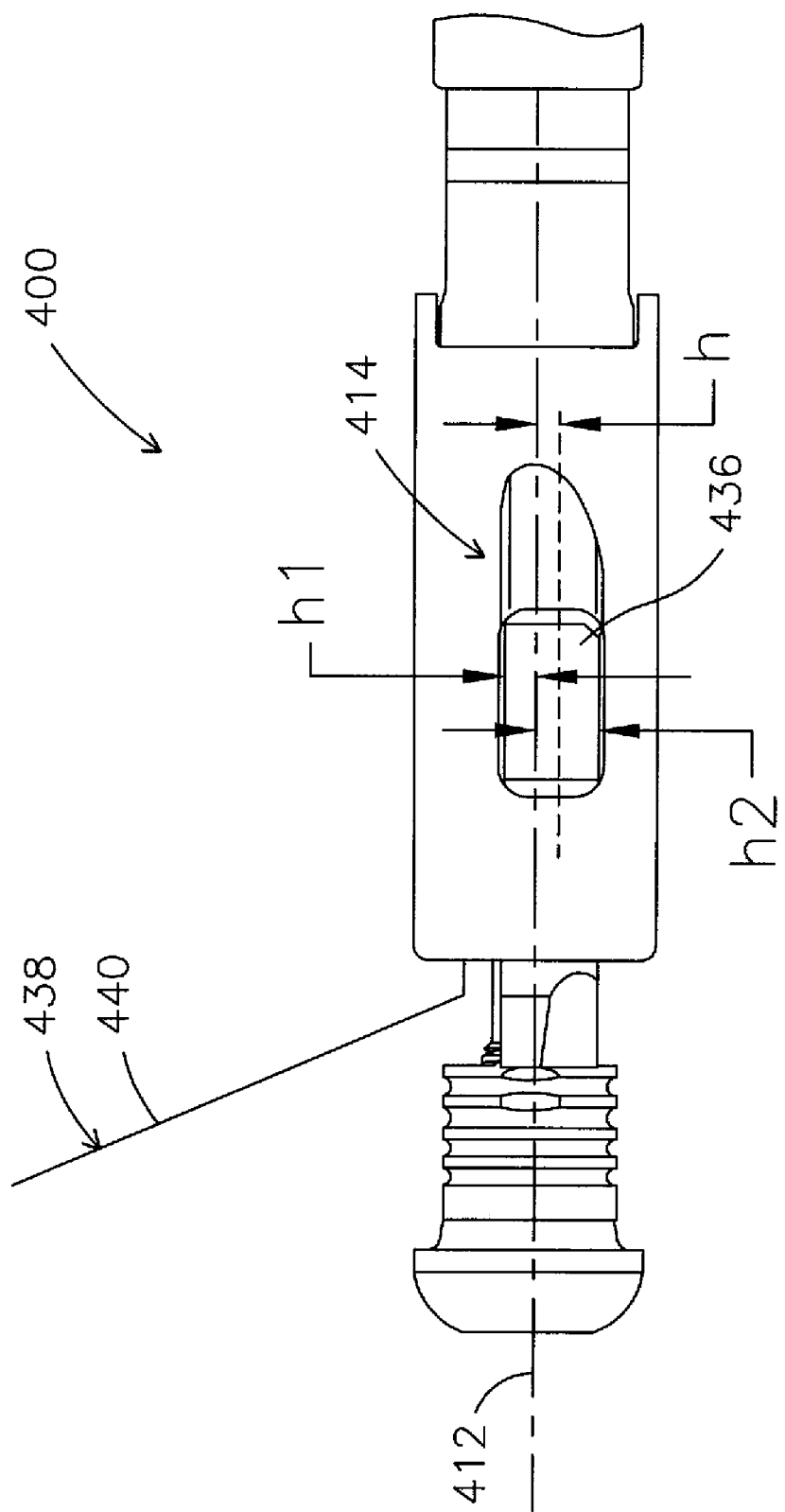
FIG. 4 is a top, plan view of yet another embodiment of an anchoring device that is made in accordance with the concepts of the present invention.

While the anchoring devices 100, 200 that are discussed above have generally concentrically and symmetrically located features relative to, e.g., the longitudinal axis 112, 212, other embodiments may have one or more of the elongated projections positioned at an offset dimension from the longitudinal axis. For example, and to illustrate this concept more clearly, FIG. 4 illustrates another embodiment of an anchoring device 400 that is made in accordance with the present invention. Here, it is seen that the anchoring device 400 includes a longitudinal axis 412, as well as an aperture 414, and an elongated projection 436. Both the aperture 414 and the elongated projection 436 are located an offset distance (h) from the longitudinal axis 412. More particularly, it is seen in the example of FIG. 4 that the position of the aperture 414 is determined in accordance with the general dimensions (e.g., first offset dimension (h1), and second offset dimension (h2)) of the elongated projection 436. The offset distance (h), as well as the first offset dimension (h1), and the second offset dimension h2 can be employed on any of the embodiments of the anchoring device 100, 200, 400 disclosed and discussed herein. In one example, the offset distance (h) is provided in the anchoring device 400 so as to provide only one loop 440 of the suture material 438.

Figure 5:
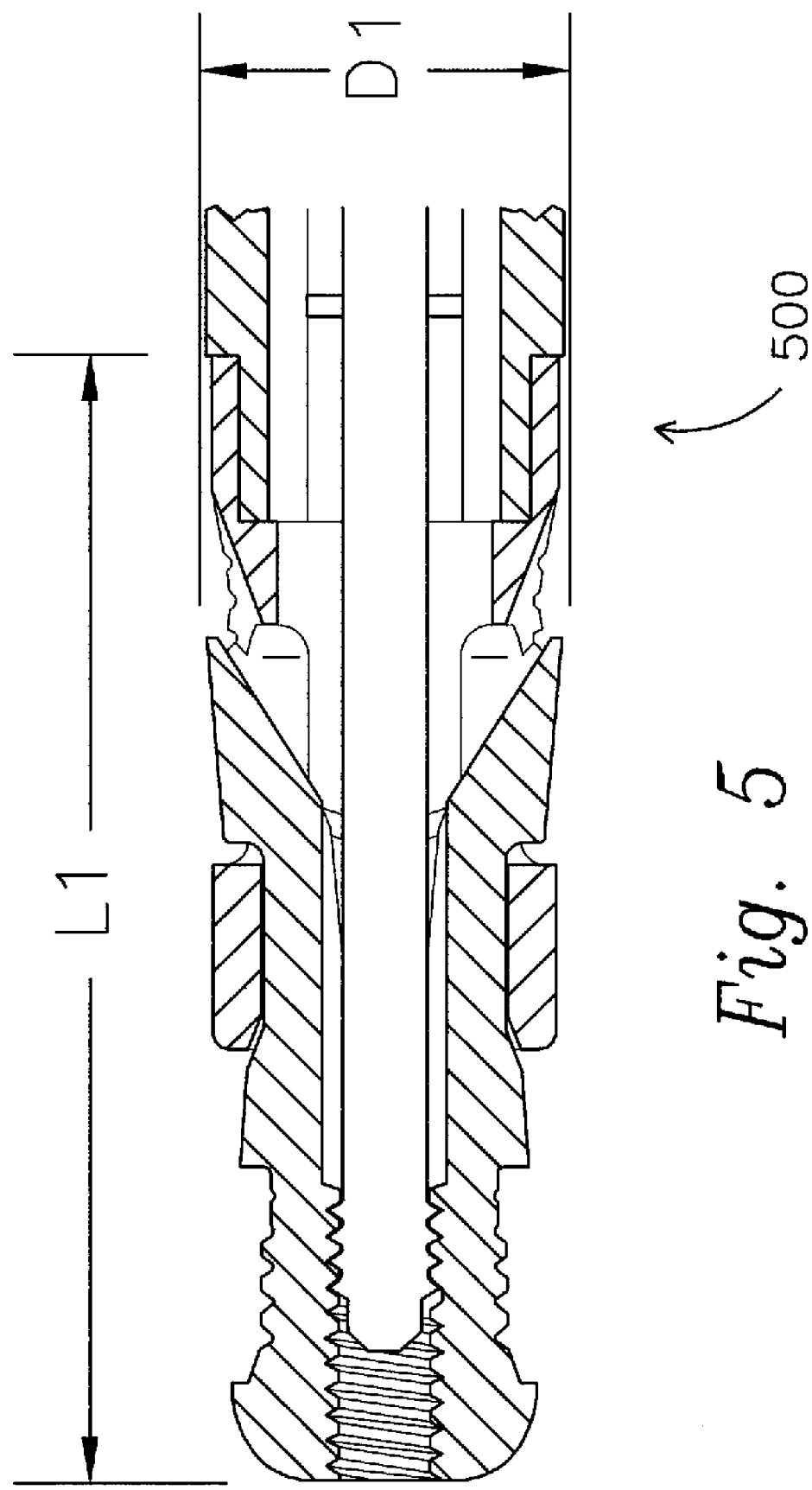
FIG. 5 is a cross-sectional, side, plan view of an anchoring device, like the anchoring devices of FIGS. 1-4 in a suture-unlocked position.
Figure 6:
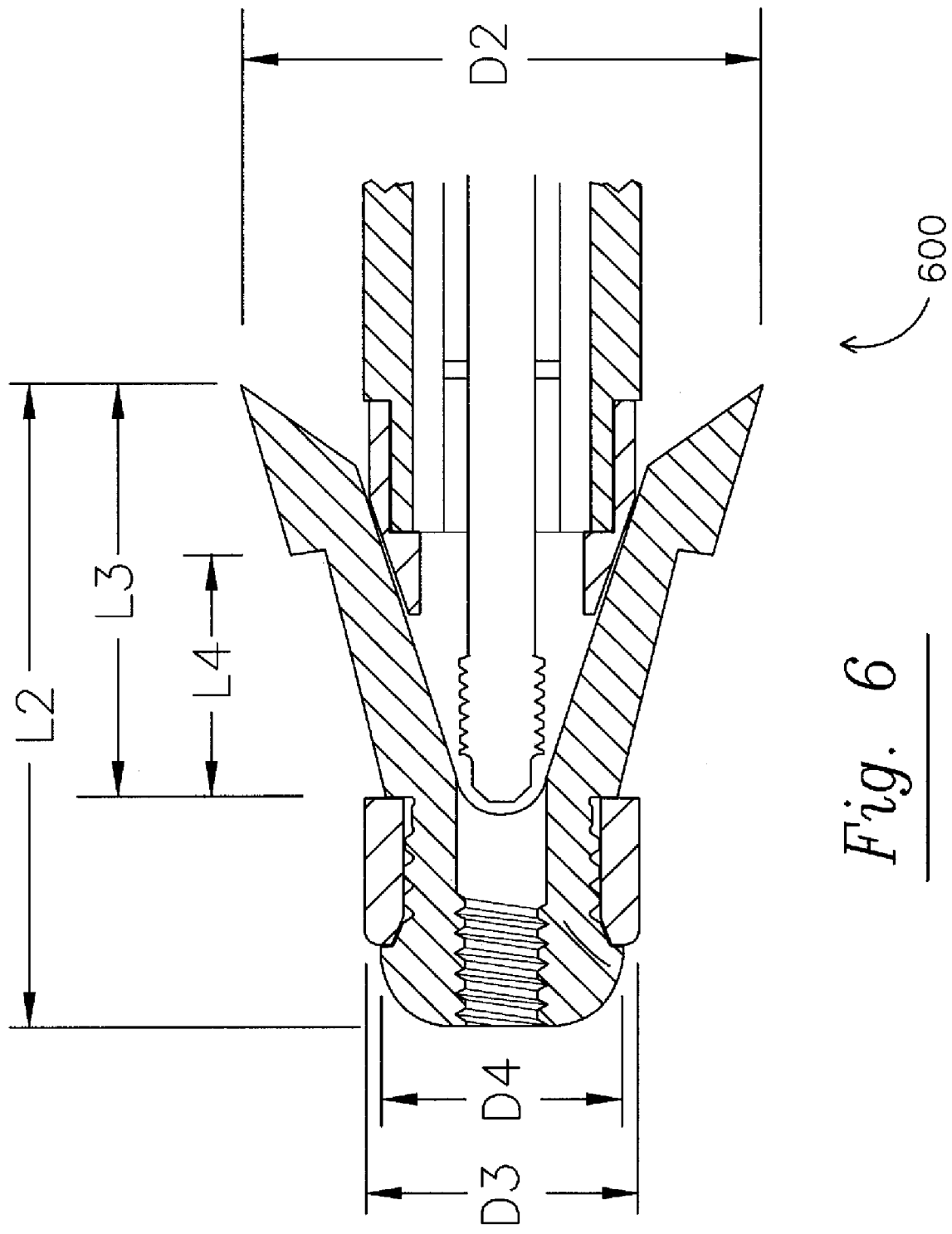
FIG. 6 is a cross-sectional, side, plan view of an anchoring device, like the anchoring devices of FIGS. 1-4 in a suture-locked position.

In view of the foregoing, and discussing some of the general features of the anchoring devices that are of the type suited for use as the anchoring devices described herein, FIGS. 5 and 6 illustrate examples of an anchoring device in a suture-unlocked position 500, and a suture-locked position 600. It is seen in FIG. 5 that the length (L1) of the anchoring devices in the suture-unlocked position 500 is from about 12 mm to about 17 mm. It is seen in FIG. 6 that the length (L2) of the anchoring device in the suture-locked position 600 is from about 9 mm to about 11 mm, and that the elongated projections may have a length (L3) from about 4 mm to about 10 mm, with a portion of the elongated projections having a length (L4) from about 2 mm to about 5 mm.

The unemployed diameter (D1), the "first dimension," at the proximal end of the anchoring device is from about 4 mm to 6 mm, and the deployed diameter (D2), the "second dimension," is from about 6 mm to about 9 mm. The diameter (D3) of the outer member at the distal end is from about 3 mm to about 5 mm, and the diameter (D4) of the inner member at the distal end is from about 2 mm to about 4 mm. All of these dimensions, however, are provided as non-limiting examples and is not meant to limit the scope, content, or concepts of the present disclosure. That is, certain ones of the dimensions discussed immediately above, when applied to other embodiments the anchoring devices, may change with respect to other dimension, pieces, and aspects of the present invention.

Figure 7:
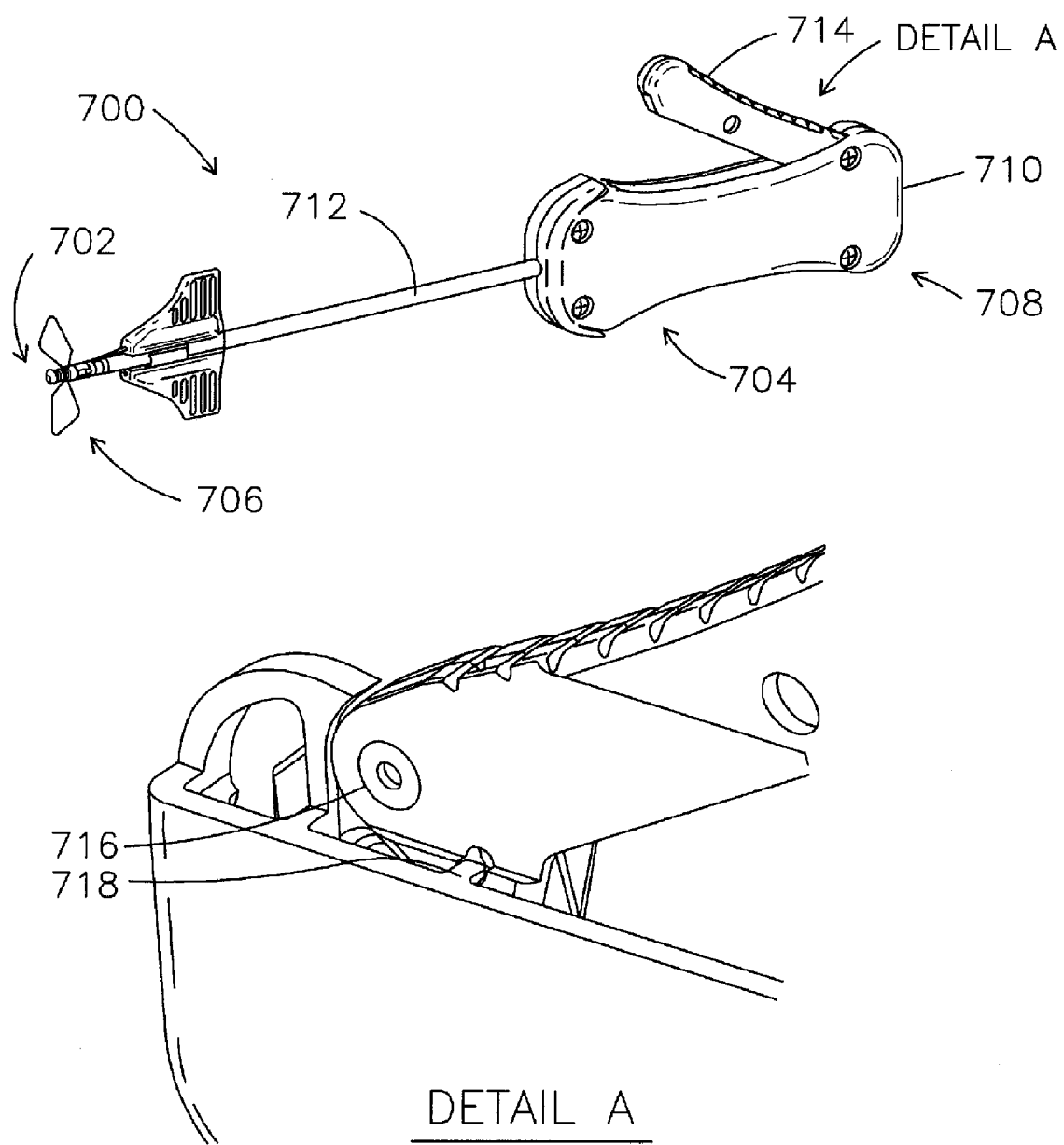
FIG. 7 is a perspective view of an embodiment of a system that is used to deploy an anchoring device such as the anchoring devices of FIGS. 1-6.

Discussing generally an implementation of the anchoring devices such as the anchoring devices 100, 200, 400, reference is made to FIG. 7, which illustrates an example of a system 700 that is used to deploy the anchoring devices disclosed herein. To facilitate its use, an anchoring device 702 is situated on an actuator device 704 that has a distal end 706, and a proximal end 708. More particularly, the anchoring device 702 is positioned on the distal end 706 so as to engage a mandrel (not shown). The actuator device 704 further includes a handle 710 and an elongated shaft 712 that houses the mandrel therein.

The operation of the actuator device 704, and the general steps of its implementation during a surgical procedure, are performed when the user has property passed the suture material through the target tissue, inserted the anchor device into a pre-formed hole in a bone, and applied sufficient tension to the suture material so as to justify deploying the anchor device, and as one consequence, knotlessly securing the suture material (or tissue) to the bone. Actuator device 704 comprises a trigger 714, and a drive mechanism (not shown) that is attached to the proximal end 708 of the elongated shaft 712. The drive mechanism, while not shown in the figures, may include levers, pivots, rollers, joints, and other mechanisms that are arranged together to provide longitudinal movement of the mandrel (not shown), and thus cause the relative movement of the parts of the anchoring device (e.g., the inner and outer members) as discussed in detail above.

For example, the actuator device 704 may include the trigger 714 and a pivot 716 that couples the trigger 714 to the drive mechanism (not shown). The actuator device 704 may also include a detent 718 that engages the trigger 714 in a manner that prevents premature actuation of the device. In one example, the detent 718 extends from part of the handle 710 into the trigger 714 a distance, which is selected based on an amount of force desired to fully engage the trigger 714 and deploy the anchoring device.

In one embodiment, depressing the trigger 714 exerts a proximally directed force that causes the relative movement of the inner member with respect to the outer member. In one example, the drive mechanism is configured to pull the inner member toward the handle 710 with the mandrel. This, in turn, causes the elongated projections to expand into the cancellous bone, and in one particular embodiment causes the mandrel to frangibly disconnect from the inner member based on a threshold force.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

While the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A knotless suture anchor for securing suture material beneath a cortical layer of a bone, comprising:
    an outer member comprising an outer axial lumen comprising a cylindrical inner suture surface extending along and encircling a longitudinal axis; and
    an elongated inner member movable within the outer axial lumen between a suture-unlocked position and a suture-locked position;
    a distal portion of the elongated inner member comprising an outer suture surface extending coaxially with said inner suture surface and an inner axial lumen being defined by an inner surface of the distal portion of the elongated inner member, the inner surface of the distal portion of the elongated inner member comprising a frangible portion configured to engage a mandrel, the mandrel configured to exert a force required to move the elongated inner member from the suture-unlocked position to the suture-locked position;
    a proximal portion of the elongated inner member extending away from the distal portion of the elongated inner member, the proximal portion comprising a proximal end having an outer dimension that increases in relation to the longitudinal axis when the elongated inner member is moved from the suture-unlocked position to the suture-locked position; and
    a filament extending along a path extending through the outer axial lumen and between the inner suture surface and the outer suture surface, in said suture-unlocked position the outer suture surface is positioned distal said inner suture surface and in said suture-locked position the filament is compressed between the outer suture surface and the inner suture surface locking the filament.

2. A knotless suture anchor according to claim 1, where the frangible portion comprises a material disengagement portion configured to disengage from the elongated inner member when the elongated inner member is positioned in the suture-locked position.

3. A knotless suture anchor according to claim 2, wherein the material engagement portion comprises a plurality of threads that engage the mandrel.

4. A knotless suture anchor according to claim 3, wherein one or more of the threads disengages from the elongated inner member when the elongated inner member is positioned in the suture-locked position.

5. A knotless suture anchor according to claim 1, wherein the proximal portion comprises at least one projection that terminates at the proximal end.

6. A knotless suture anchor according to claim 5, wherein the at least one projection comprises a distal facing shoulder that engages a portion of the outer member in the suture-locked position.

7. A knotless suture anchor according to claim 6, wherein each projection is passed through an aperture in the outer member when the elongated inner member is in the suture-locked position.

8. A suture anchor, comprising:
an outer member comprising an outer axial lumen comprising an inner suture surface extending along a longitudinal axis; and
an elongated inner member adapted to be movable along the longitudinal axis between at least two positions within the outer axial lumen, two of the positions being a suture-unlocked position and a suture-locked position;
a distal portion of the elongated inner member comprising an outer suture surface, and an inner axial lumen defined by an inner surface of the distal portion of the elongated inner member, the inner surface of the distal portion of the elongated inner member comprising a frangible portion, the frangible portion comprising a plurality of threads; and
at least one longitudinal projection extending from the distal portion of the elongated inner member along the longitudinal axis and terminating at a proximal end of the elongated inner member, the proximal end having an outer dimension that increases relative to the longitudinal axis when the elongated inner member is moved from the suture-unlocked position to the suture-locked position;
wherein the plurality of threads are configured to engage a mandrel that effectuates the movement between the suture-unlocked position and the suture-locked position in a manner that engages a suture material between the outer suture surface and the inner suture surface in the suture-locked position, and
wherein the at least one longitudinal projection comprises a first distal facing shoulder on an external surface of the elongated inner member and the outer member further comprises a first proximal facing shoulder, the first distal facing shoulder engaging with the first proximal facing shoulder in said suture-locked position.

9. A suture anchor according to claim 8, wherein the outer suture surface and the inner suture surface engage and compress at least about 2 mm of a filament in the suture-locked position.

10. A suture anchor according to claim 8, wherein the outer suture surface comprises a plurality of suture compression projections extending radially outwardly from the longitudinal axis.

11. A suture anchor according to claim 8, wherein the outer member comprises an aperture having a ramped surface that engages each of the at least one longitudinal projection in the suture-locked position in a manner that increases the outer dimension relative to the longitudinal axis.

12. A suture anchor according to claim 11, wherein the increase in the outer dimension between the suture-unlocked position and the suture-locked position is at least about 2 mm.

13. A suture anchor according to claim 11, wherein the elongated inner member further comprises a proximal facing shoulder positioned at a distal end of the inner suture surface, the proximal facing shoulder being urged against a distal end of the outer member when the elongated inner member is moved into the suture-locked position.

14. An anchoring system, comprising:
an inserter comprising a distal end having a mandrel and a proximal end having an actuator device, the actuator device being coupled to the mandrel in a manner that is configured to move the mandrel from a suture-unlocked position to a suture-locked position; and
a knotless suture anchor coupled to the mandrel, the knotless suture anchor comprising an elongated inner member and an outer member in surrounding relation to the elongated inner member,
the outer member comprising an outer axial lumen receiving the elongated inner member and allowing the elongated inner member to be movable between at least two positions, two of the positions being the suture-unlocked position and the suture-locked position,
a cylindrical inner suture surface of the outer member extending along and encircling a longitudinal axis of the knotless suture anchor,
a distal portion of the elongated inner member comprising an outer suture surface extending coaxially with said inner suture surface and an inner axial lumen defined by an inner surface of the distal portion of the elongated inner member, the inner surface of the distal portion of the elongated inner member comprising a frangible portion configured to engage the mandrel, the mandrel configured to exert a force required to move the elongated inner member from the suture-unlocked position to the suture-locked position, a suture material being engaged between the inner suture surface and the outer suture surface when the elongated inner member is in the suture-locked position,
a proximal portion of the elongated inner member extending away from the distal portion of the elongated inner member, the proximal portion comprising a proximal end having an outer dimension that increases in relation to the longitudinal axis when the elongated inner member is moved from the suture-unlocked position to the suture-locked position, and
a suture loading mechanism coupled to the inserter, the suture loading mechanism including filaments extending through the outer axial lumen and between the inner suture surface and the outer suture surface.

15. An anchoring system according to claim 14, wherein the actuator device comprises a trigger, and a drive mechanism actuated by the trigger so as to change the mandrel from the suture-unlocked position to the suture-locked position.

16. An anchoring system according to claim 15, wherein the actuator device further comprises a handle that includes the trigger and a detent coupled to the trigger so as to prevent premature movement of the mandrel.

17. An anchoring system according to claim 14, wherein the frangible connection comprises a material disengagement portion configured to disengage from the elongated inner member when the elongated inner member is positioned in the suture-locked position.

18. An anchoring system according to claim 14, wherein the elongated inner member further comprises a proximal facing shoulder positioned at a distal end of the inner suture surface, the proximal facing shoulder being urged against a distal end of the outer member when the elongated inner member is moved into the suture-locked position.

* * * * *